United States Patent [19]
Bunnell

[11] Patent Number: 5,181,525
[45] Date of Patent: Jan. 26, 1993

[54] SCOLIOSIS SCREENING DEVICE

[76] Inventor: William P. Bunnell, 9 Crestfield Rd., Wilmington, Del. 19810

[21] Appl. No.: 343,053

[22] Filed: Apr. 25, 1989

Related U.S. Application Data

[63] Continuation of Ser. No. 598,531, Apr. 9, 1984, abandoned, which is a continuation of Ser. No. 417,865, Sep. 14, 1982, abandoned.

[51] Int. Cl.5 .......................................... A61B 05/103
[52] U.S. Cl. .................................................. 128/781
[58] Field of Search .................. 128/781, 774; 33/512

[56] References Cited

U.S. PATENT DOCUMENTS

| | | | |
|---|---|---|---|
| 2,067,474 | 1/1937 | Carbanava | 33/365 |
| 2,168,885 | 8/1939 | Rickenbach et al. | 33/365 |
| 3,465,450 | 9/1969 | Hamilton | 33/174 D |
| 3,774,314 | 11/1973 | Youngs | 33/365 X |
| 4,444,204 | 4/1984 | Bryant et al. | 128/781 |

FOREIGN PATENT DOCUMENTS

| | | | |
|---|---|---|---|
| 685277 | 9/1979 | U.S.S.R. | 128/781 |

*Primary Examiner*—Kyle L. Howell
*Assistant Examiner*—John C. Hanley
*Attorney, Agent, or Firm*—Mortenson & Uebler

[57] ABSTRACT

The disease scoliosis is a rotational deformity of the spine and ribs, characterized by both lateral curvature and vertebral rotation. Idiopathic genetic scoliosis occurs about seven time more frequently in the female than in the male and accounts for about 80% of all cases of the disease. The deformity first appears in infants, juveniles or adolescents generally, and many school health programs in this country have screening programs for the early detection of the disease. On detection, the patient is referred to a specialist for treatment. Presently, however, over-referral of great numbers of children with very mild curvatures which do not require treatment is causing a large number of unnecessary x-rays and needless lost time and expense. The invention disclosed herein is a simple and convenient device for measuring the clinical deformity in patients with scoliosis which establishes objective criteria for screening and which can significantly reduce the number of over-referrals.

10 Claims, 2 Drawing Sheets

SCOLIOSIS SCREENING DEVICE

CROSS-REFERENCE TO RELATED APPLICATION

This application is a continuation of prior copending application Ser. No. 06/598,531, filed Apr. 9, 1984 which was a continuation of Ser. No. 06/417,865, filed Sep. 14, 1982, now abandoned.

BACKGROUND OF THE INVENTION

This invention relates to a device for measuring the degree of spinal deformity in patients having scoliosis. The widespread use of school screening programs for the early detection of spinal deformity has significantly reduced the need for spinal fusion because effective nonoperative measures can be used if the deformity is found before it becomes severe. However, a problem has been created by these programs, namely, over-referral of great numbers of children with very mild curvatures which do not require treatment.

Because no objective criteria for referral have been established, the number of children referred by the screening process depends upon individual experience or technique of the referring nurse or technician. There is a wide variability in the reported incidence of scoliosis in school children, ranging from 1 to 16 percent. These figures must be viewed in relationship to the accepted incidence of scoliosis in the adult population, which is approximately 2 percent, and the estimated number who actually require treatment, which is 0.2 percent. Such over-referral clearly results in unnecessary x-ray examinations and needless expenditure of health care dollars and points to the need for a more selective screening method.

A number of clinical methods have been used in the past to document the clinical deformity in scoliosis. The most commonly used method employs a spirit level and ruler to measure the height of the "rib hump" at the apex of the deformity. This has the disadvantage of being cumbersome, and also fails to take into account the size of the patient in determining the significance of the rib deformity.

Contour devices may be used to transfer the outline of the deformity to a sheet of paper or back of an x-ray folder. These methods are somewhat inconvenient and have not gained widespread use.

More recently, moire fringe topography has been used as a method for both screening and follow-up examinations. While the method may be quite accurate, the apparatus is costly and requires space for a permanent setup, personnel to operate it, and, ideally, a computer to analyze and store information.

SUMMARY OF THE INVENTION

A device and method are provided for measuring the angle of trunk rotation in patients who have scoliosis, the device comprising:

a U-tube filled with a fluid and containing
a ball indicator
the tube being encased in a groove in a backing plate, the edge of the plate during angle measurement which contacts the patient having an indentation therein which substantially conforms to the patient's back and spinal column,
the plate having indicia thereon to indicate the angle of trunk rotation, the angle being shown by the position of the ball indicator in the U-tube.

Preferably the fluid is water, the ball is made of stainless steel, the plate is polystyrene and the U-tube is affixed to the plate within a groove in the plate by an adhesive.

Figure 1:
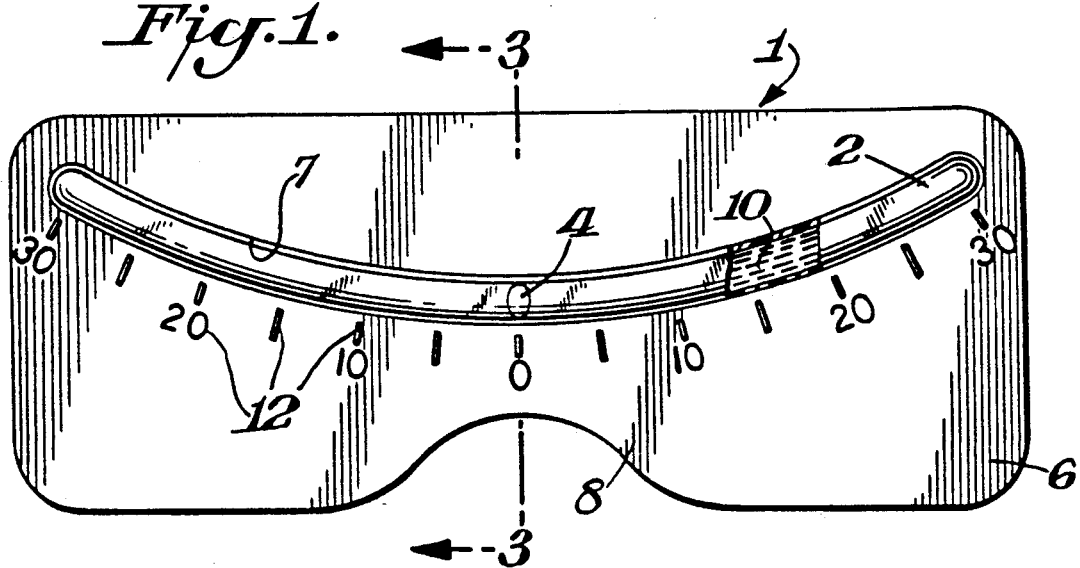
FIG. 1 is a front elevational view of the scoliosis screening device of this invention, partly broken away.

DETAILED DESCRIPTION OF THE INVENTION AND PREFERRED EMBODIMENTS WITH REFERENCE TO THE DRAWINGS

The Scoliosis Research Society has defined the angle of thoracic inclination as follows: "the angle between the horizontal and a plane across the posterior rib cage at the greatest prominence of a rib hump". This may be appropriate for thoracic curves but does not described the type of deformity which occurs in thoracolumbar and lumbar curves. For purposes of this invention, the angle of trunk rotation is defined as: "the angle between the horizontal and a plane across the posterior trunk at the point or points of maximum deformity." If a minimum significant degree of trunk rotation could be defined, many unnecessary referrals of minor curves could potentially be eliminated and thus the specificity of the screening process increased. This invention provides that definition. Measurement of the angle of trunk rotation is made with the screening device of this invention which comprises an inclinometer-type instrument having a U-tube filled with fluid to dampen the motion of a ball within the tube which seeks the lowest point in the tube, the tube being encased in a plate with the bottom edge of the plate having an indentation which conforms to a patient's back and spinal column, the plate having indicia thereon representing degrees of rotation.

The measurement is taken by having the patient bend forward to expose the point of maximum deformity, which should be viewed at eye level from behind the patient. The device is laid across the apex of the deformity, perpendicular to the long axis of the body, and the angle of inclination read directly from the device and recorded. The placement of the device will depend on the curve pattern and is determined with the patient bent forward.

Two measurements are required in patients with a double major curve pattern; one with the patient bent forward to expose the thoracic spine, and the second with the patient bent even further forward to expose the lumbar spine.

A clinical summary sheet was used to record clinical data. The top one-third of the chart contained demographic data, curve characteristics, and treatment history which remain unchanged from visit to visit. The middle one-third contained clinical data, including data of visit, height degree of breast development, and the angle of trunk rotation. The lower one-third of the sheet provided for recording radiographic data and the plan for the next visit. All of the essential information for several clinic visits can be provided on a single summary sheet which is efficient and convenient to maintain.

An ongoing prospective study was conducted which included 719 patients with the diagnosis of scoliosis who had already been referred for medical evaluation. On record are 1,965 clinical examinations and 1,203 roentgenographic examinations. Follow-up ranged from zero to fifty-one months.

Two hundred and thirty-two patients had only one visit; 191 patients had two visits; 102 patients had three visits; and 194 patients had four or more visits recorded.

The etiology of scoliosis was idiopathic in 675 patients and congenital or "miscellaneous" in 44 patients. There were 318 thoracic curves (45 percent), 127 thoracolumbar curves (18 percent), 118 lumbar curves (16 percent), and 156 double major curves (21 percent). Four hundred sixty eight patients were under observation only, while 234 patients were being treated in a brace. Seventeen patients had a posterior spinal fusion.

All data was collected and stored on computer for later retrieval and correlation.

Five degrees of trunk rotation is the minimum significant angle which should be present to justify referral from a screening program. This amount of rotation may be easily detected by paramedical personnel using the device of this invention.

The angle of trunk rotation was compared to the degree of spinal curvature in each of the 719 patients tested. There is a very general correlation between the angle of trunk rotation and the degree of curvature, with a very wide range in rotation for any given degree of curvature.

Curvatures of less than 20 degrees were noted in 76 percent of cases referred from screening programs. Since curves of less than 20 degrees are rarely treated, these patients should not have been selected by the screening process. Of those curves under 20 degrees, 40 percent had angles of trunk rotation less than 5 degrees, and 60 percent had angles greater than 5 degrees. If the screening personnel had used the device of this invention and required 5 degrees of trunk rotation as the basis for selection, 40 percent of the unnecessary referrals could have been eliminated.

It is also important to consider those patients with curves of more than 20 degrees who have angles of trunk rotation less than 5 degrees. These patients represent false negative screening examinations. There were 15 such cases in the 719 patients tested, for a false negative rate of 2.1 percent of the patients referred. Only four of these curves were greater than 25 degrees, and none were idiopathic. If 10 percent of all children screened were referred and thus became the basis of this study, then approximately 7000 children were screened, and the false negative actual rate for the screening program was 0.2 per cent.

If the minimum significant angle of rotation were increased to 6 degrees, nearly 60 percent of unnecessary referrals could be eliminated, but the false negative screening rate would double. For this reason, it is believed that the minimum significant angle should be 5 degrees in practice.

The measurement of the angle of trunk rotation was used as a monitoring device to detect curve progression on follow-up visits without the use of radiographs. This is useful in young patients with mild degrees of curvature which frequently are not progressive but which should be followed until the patient reaches skeletal maturity.

A change in the angle of trunk rotation of 3 degrees or more was considered significant. Two degrees or less was considered to be within the measurement error. This was arbitrarily chosen early in the study on clinical grounds and later verified by taking the largest difference in the measurement of trunk rotation on patients with multiple visits. The average difference was 1.8 degrees from visit to visit, with a range of 0 to 6 degrees.

A 12 percent false positive rate was experienced; that is, an increase in the angle of trunk rotation of 3 degrees or more was measured on subsequent visits, but a repeat radiograph showed less than 6 degrees of change.

In 111 patients, changes in curvatures of more than 5 degrees were noted radiographically. Of these, forty-six showed a spontaneous decrease in curvature with no treatment. The angle of trunk rotation was unchanged in most of these patients. Twenty-seven patients had an increase of greater than 5 degrees in their curvature, and this was detected clinically by an increase of 3 degrees or more in their angle of trunk rotation. Seventeen patients had an increase in curvature of greater than 5 degrees which was not detected by an increase in the angle of trunk rotation.

A review of those curves in which progression was undetected by clinical measurement shows that five patients still had curves of less than 20 degrees even after progression. Two patients were wearing a brace; one had a non-idiopathic diagnosis, and four additional patients had both a non-idiopathic diagnosis and wore a brace. Three patients had idiopathic scoliosis with double major curve patterns. Thus, one-half of the progressive curves which occured in brace patients were undetected, one-half of the progressive non-idiopathic scoliosis was undetected, and one-half of the idiopathic double major curve patterns which progressed were also undetected by the clinical measurement.

Of twenty-seven progressive curves were detected, eighteen had curve progression on the radiograph averaging 12.9 degrees. Of the remaining nine patients, four were wearing a brace; two had a non-idiopathic diagnosis; and one was in a brace with a non-idiopathic diagnosis. Only two curves remained under 20 degrees following the progression.

There are several advantages to using this method both for screening and for following spinal deformity. Its convenience and simplicity increase the likelihood that it will be used regularly in contrast to more cumbersome or costly methods which are at greater risk of falling into disuse. The method also provides an objective standard by which to recommend referral from screening programs. This is especially helpful for less experienced personnel and, as shown by the data, can significantly reduce the number of unnecessary referrals. The method can also allow a reduction in the number of x-rays required in the follow-up of patients with mild scoliosis. All of this can result in a significant savings of health care dollars.

Measurement on follow-up examination provides objective clinical information rather than just "eyeball recall", and if the clinical summary sheet is used to record other growth parameters, a much more complete and satisfactory follow-up examination can be easily accomplished.

The angle of trunk rotation provides a much more useful measurement and description of the clinical deformity than x-ray measurements. Since measuring "angle" rather than "height" takes the size (width) of the patient into account, the deformity for any given degree of trunk rotation will look virtually identical in every patient, as opposed to either x-ray measurements or the height of rib hump. This measurement could also help to standardize the "cosmetic" indications for surgery. In addition, this method allows for objective measurement of the improvement in clinical deformity achieved by bracing or surgical treatment.

The use of 5 degrees as the minimum significant angle of rotation is appropriate in that it is sensitive enough to produce a false negative rate of only 0.2 percent, and specific enough to eliminate nearly one-half of the unnecessary referrals generated by current screening techniques.

A detailed description of the scoliosis screening device of this invention is best provided with reference to the appended drawings. In FIG. 1, in front elevation, the screening device 1 is shown comprising a fluid filled U-tube 2 containing indicator ball 4 which seeks the lowest point in the tube under the force of gravity. The tube is preferably glass, the ball is preferably stainless steel and the fluid is preferably water. Plate 6 contains groove 7 into which is placed the U-tube 2 and anchored therein, preferably with an adhesive. The indentation 8 in plate 6 conforms to a patient's back and spinal column during measurement of the trunk rotation angle. Plate 6 has indicia 12 thereon which indicate the angle of rotation on visual inspection. In the portion of FIG. 1 which is broken away, the fluid 10 in the U-tube 2 is shown. Plate 6 is preferably polystyrene but many other materials could be used.

Figure 2:
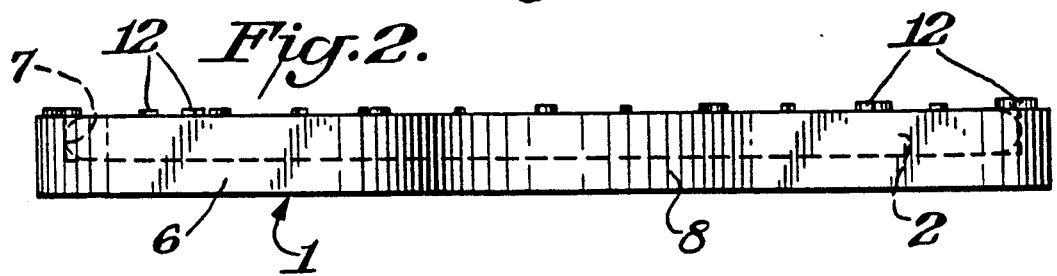
FIG. 2 is a bottom plan view of the device.

FIG. 2 is a bottom plan view of the device 1 showing tube 2 in phantom set into groove 7 in plate 6, the plate having bottom indentation 8 and raised indicia 12 thereon. It will be clear to one skilled in the art that the indicia 12 need not be raised but can be placed on plate 6 by any convenient method.

Figure 3:
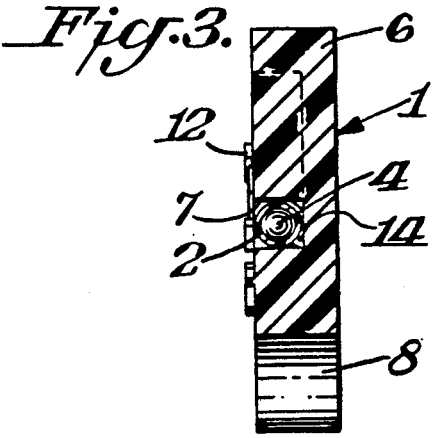
FIG. 3 is a cross-sectional view of the screening device taken along the line 3—3 of FIG. 1.

FIG. 3, taken along line 3—3 of FIG. 1, shows the device 1 in cross-section wherein tube 2 containing indicator ball 4 is held in groove 7 in plate 6 by adhesive 14. While an adhesive is preferred, other means for securing the U-tube to the plate 6 will be readily apparent to one skilled in this art. Indicia 12 and indentation 8 are included in FIG. 3 for completeness.

Figure 4:
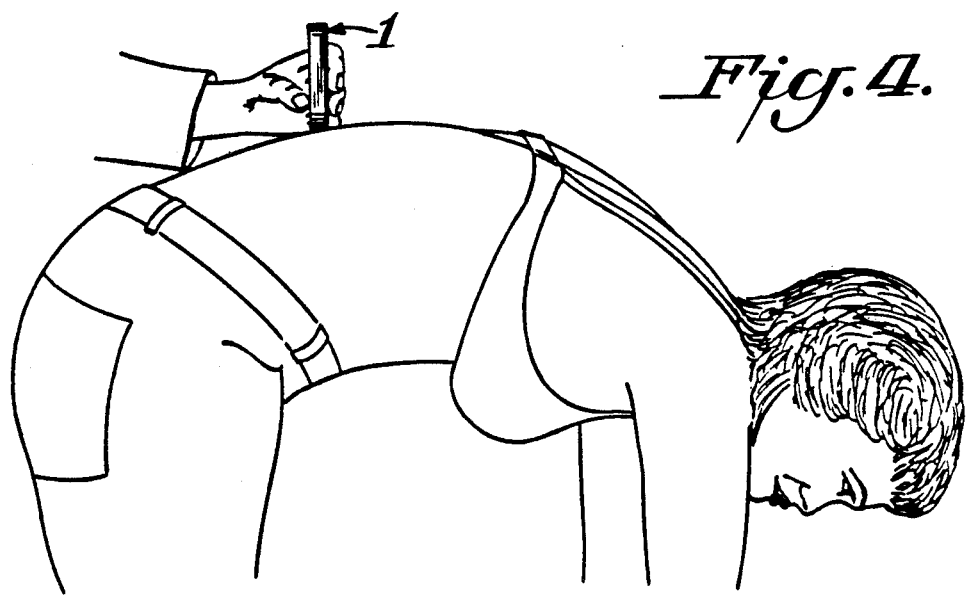
FIG. 4 is a side elevational view showing a clinician measuring the angle of trunk rotation of a patient.

FIG. 4 shows a side elevation of the device 1 of this invention being used by a clinician to measure the degree of trunk rotation of a patient.

Figure 5:
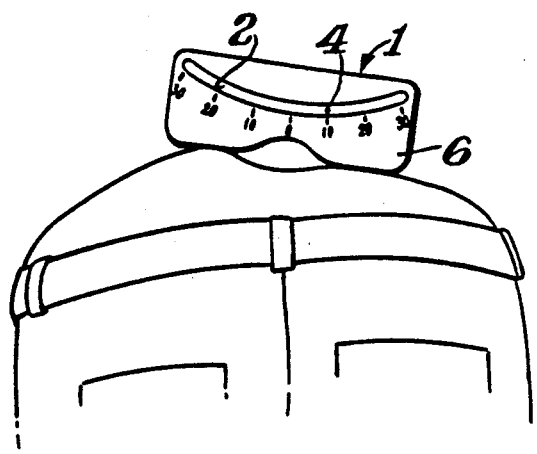
FIG. 5 is a rear elevational view showing the device used to measure the angle of trunk rotation of a patient, that angle being 10° C. in this figure.

FIG. 5 shows a rear elevation of the same patient as shown in FIG. 4 with the device 1 in place, wherein ball indicator 4 in U-tube 2 indicates a 10° angle of trunk rotation in this patient.

Figure 6:
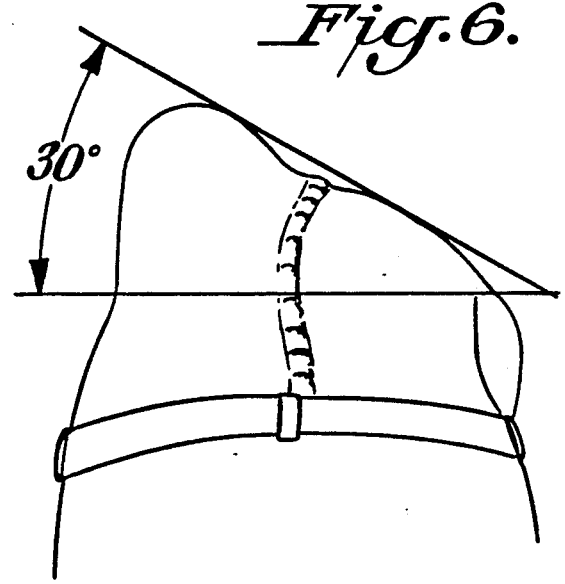
FIG. 6 is a rear elevational view of a patient whose angle of trunk rotation is 30°.

FIG. 6 shows a patient having an advanced 30° angle of trunk rotation.

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

I claim:

1. A device for measuring the angle of trunk rotation in a patient comprising:
   a backing plate having a U-shaped groove therein and an edge which contacts said patient during measurement, the U opening away from said edge of said plate which contacts said patient during measurement,
   a transparent U-tube affixed to said backing plate in said groove,
   said tube being filled with a fluid and containing a ball indicator,
   said edge of said plate which contacts the patient being generally straight and having a generally semi-circular indentation therein to accomodate the spinal column of the patient,
   said plate having indicia thereon to indicate the angle of trunk rotation, said angle being shown by the position of the ball indicator in said U-tube.

2. The device of claim 1 wherein said fluid is water.

3. The device of claim 1 wherein said ball is stainless steel.

4. The device of claim 1 wherein the plate is polystyrene.

5. The device of claim 1 wherein said U-tube is affixed to said plate by an adhesive.

6. The method of measuring the angle of trunk rotation in a patient comprising:
   having said patient bend forward to expose the apex of maximum deformity, viewed at eye level from behind the patient,
   laying across the apex of the deformity, substantially perpendicular to the long axis of the body, and reading the angle of rotation directly from, a device comprising:
   a backing plate having a U-shaped groove therein and an edge which contacts said patient during measurement, the U opening away from said edge of said plate which contacts said patient during treatment,
   a transparent U-tube affixed to said backing plate in said groove,
   said tube being filled with a fluid and containing a ball indicator,
   said edge of said plate which contacts the patient being generally straight and having a generally semi-circular indentation therein to accomodate the spinal column of the patient,
   said plate having indicia thereon to indicate the angle of trunk rotation, said angle being shown by the position of the ball indicator in said U-tube,
   whereby, when placed on said patient's back, the angle of trunk rotation is read directly in a single procedure, said indentation providing means for avoiding interference in such measurement by the patient's spinal column.

7. The method of claim 6 wherein said fluid is water.

8. The method of claim 6 wherein said ball is stainless steel.

9. The method of claim 6 wherein the plate is polystyrene.

10. The method of claim 6 wherein said U-tube is affixed to said plate by an adhesive.

* * * * *